(12) United States Patent
Hilty (10) Patent No.: US 9,067,062 B2
(45) Date of Patent: Jun. 30, 2015

(54) IRRADIATION/COOLING COMBINATION FOR APPLICATION IN PHOTODYNAMIC THERAPY

(76) Inventor: Norbert Hilty, Schaan (LI)

(*) Notice: Subject to any disclaimer, the term of this patent is extended or adjusted under 35 U.S.C. 154(b) by 758 days.

(21) Appl. No.: 13/256,244

(22) PCT Filed: Mar. 17, 2010

(86) PCT No.: PCT/EP2010/053427
§ 371 (c)(1),
(2), (4) Date: Sep. 13, 2011

(87) PCT Pub. No.: WO2010/106086
PCT Pub. Date: Sep. 23, 2010

(65) Prior Publication Data
US 2012/0004711 A1    Jan. 5, 2012

(30) Foreign Application Priority Data
Mar. 18, 2009  (EP) ..................... 09155532

(51) Int. Cl.
*A61N 5/06*  (2006.01)
*A61B 18/00* (2006.01)
*A61N 5/00*  (2006.01)

(52) U.S. Cl.
CPC ....... *A61N 5/062* (2013.01); *A61B 2018/00023* (2013.01); *A61N 2005/007* (2013.01)

(58) Field of Classification Search
CPC .................. A61F 2007/004; A61F 2007/0089; A61F 2007/108; A61F 7/02; A61N 2005/0644; A61N 2005/0645; A61N 2005/0648; A61N 2005/0652; A61N 2005/0659; A61N 5/0613
USPC .................................... 606/2–19; 607/88–94
See application file for complete search history.

(56) References Cited

U.S. PATENT DOCUMENTS

| | | | |
|---|---|---|---|
| 6,096,066 A | 8/2000 | Chen | |
| 6,290,713 B1 | 9/2001 | Russell | |
| 6,454,789 B1 | 9/2002 | Chen et al. | |
| 7,304,201 B2 | 12/2007 | Holloway et al. | |

(Continued)

FOREIGN PATENT DOCUMENTS

| | | |
|---|---|---|
| GB | 2408209 A | 5/2005 |
| WO | WO-97/22384 A | 6/1997 |

(Continued)

*Primary Examiner* — Aaron Roane
(74) *Attorney, Agent, or Firm* — Muncy, Geissler, Olds & Lowe, P.C.

(57) ABSTRACT

The invention relates to an irradiation-cooling combination for application in photodynamic therapy having an irradiation element (120), a cooling element (130) permeable by the emitted radiation in an irradiation pass-through direction, wherein said cooling element is designed for attachment between the irradiation element (120) and a treatment surface (160) of a patient. The cooling element (130) has an optical pass-through surface that can be cooled as an attachment to the treatment surface (160). Additional components of the invention are a first fastening device (150) for defined positioning of the irradiation-cooling combination opposite the treatment surface (160), a second fastening device (140) for attaching the irradiation element (120) on the cooling element (130), a control unit (110) and a power supply (100). The invention provides effective pain management during photodynamic therapy in connection with a mobile treatment system and larger treatment areas by means of a uniform radiation field.

15 Claims, 10 Drawing Sheets

(56) References Cited

U.S. PATENT DOCUMENTS

2003/0009205 A1   1/2003   Biel
2006/0235494 A1*  10/2006  Vanderschuit .................. 607/89
2008/0039906 A1   2/2008   Huang et al.

FOREIGN PATENT DOCUMENTS

| WO | WO-02/03876 A | 1/2002 |
| WO | WO-2007/125336 A | 11/2007 |

* cited by examiner

IRRADIATION/COOLING COMBINATION FOR APPLICATION IN PHOTODYNAMIC THERAPY

This application is a national stage of International Application No. PCT/EP2010/053427, which was filed on Mar. 17, 2010, and which claims priority to European Patent Application No. 09155532.6, which was filed in Europe on Mar. 18, 2009, and which are both herein incorporated by reference in their entirety.

The invention relates to an irradiation/cooling combination for application in photodynamic therapy according to the preamble of claim 1 and to an irradiation method for providing a homogenized radiation field at a cooled optical passage region according to the preamble of claim 14.

Photodynamic therapy (PDT) is understood to mean a method for treating tumors and other changes in the tissue using light in combination with a light-sensitive substance—a so-called photosensitizer—and oxygen present in the tissue. To this end, the patient is administered such a sensitizer or one of its metabolic precursors, which selectively enriches in the tumor. After a certain period of waiting, the tumor and the healthy tissue surrounding it are subsequently irradiated with light at a suitable wavelength. This creates cytotoxic substances as a result of photo-physical processes, which cytotoxic substances damage the tumor in a targeted fashion as a result of the tumor selectiveness of the sensitizer.

Porphyrins are predominantly used as photosensitizers, and these can be activated by irradiation with red light at a wavelength of between 630 nm and 635 nm. Currently, use is mainly made of 5-aminolevulinic acid (ALA) or the methyl ester (MALA) thereof, a metabolic precursor of protoporphyrin IX, which selectively excites porphyrin synthesis in the tumor cells. Newer sensitizers can be excited at even longer wavelengths, which is advantageous in that the PDT is effective at slightly greater depths because light at longer wavelengths has a greater penetration depth into the skin.

The damaging effect on the tumor tissue is generally based on the creation of energetically excited and very reactive singlet oxygen, which destroys the surrounding afflicted tissue by oxidation.

Both incoherent lamps, e.g. xenon or halogen lamps, and laser systems and light-emitting diodes (LEDs) were found to be suitable light sources for use within the scope of PDT. A host of different light sources are available and are used for PDT.

In the following text, the term "light" is generically used for the wavelength range of visible light and the near ultraviolet and infrared radiation.

A particularly large problem in the application of PDT is the pain that sets in the patient directly after the start of the irradiation and that sometimes is felt to be very severe. Although some users attempt to provide relief already prior to the irradiation by means of local or systemic pain treatment, the intermediate cooling of the treatment region (skin surface of the patient) with ice packs, cold sprays (e.g. ethyl chloride), gel packs, cool packs, or by air cooling by means of a ventilation device has been found hitherto to be the most efficient method for reducing pain.

As a result of the irradiation by light, there is a local heating of the treatment region and the tissue situated therebelow. The pain conduction in the nerves is initiated by the stimulation of a receptor (TRPV-1), which is activated at 41° C. under normal conditions, but already activated at 33° C. after an application of the photosensitizer.

The pain occurring during the irradiation necessitates an intervention by the medical staff carrying out the treatment in the form of temporarily optically covering the treatment region or, if necessary, an interruption in the use and the application of coolants. This increases the treatment times or even aborts the irradiation.

The apparatuses and items of equipment known from the prior art do not comprise an integrated pain management system, which is in direct contact with the skin surface. Ventilators in the casing of the PDT lamp, as implemented e.g. in the model "Omnilux" from "Photo Therapeutics Ltd." (Altrincham, UK), should serve for pain reduction, but were found in practical application not to be efficient enough to attain sufficient pain alleviation in the patient.

Equipment currently used for PDT usually comprises an irradiation element that is attached to an articulated arm, e.g. the models "Aktilite CL16" and "Aktilite CL128" from "Photocure ASA" (Oslo, Norway) or "Waldmann 1200L" and "Waldmann 450L" from "Herbert Waldmann GmbH & Co. KG" (Villingen-Schwenningen, Germany). The articulated arm in turn is located on a drivable stand or can be attached to e.g. a table top by means of a holder.

In conjunction with the massive power supply unit, control equipment and articulated arm, the irradiation element forms an unwieldy and spatially fixed apparatus, which essentially is only suitable for application in medical treatment rooms. The patient is subjected to the treatment in a resting, e.g. lying or sitting, position. The mobility of the patient is thereby completely limited during the treatment.

A further disadvantage in the application of the aforementioned equipment type for PDT is the inhomogeneity of the radiation field impinging on the treatment region. The substantially planar arrangement of the discrete light sources of the irradiation element brings about uneven irradiation on the generally convexly arced treatment region, i.e. different areal segments are subjected to different light doses. This effect increases with the size of the area to be treated.

The treatment region specified for the "Aktilite CL16" equipment is merely approximately 20 cm$^2$ as a result of the abovementioned reasons.

The irradiation element of the aforementioned type of equipment moreover is not placed against the treatment region, e.g. the skin surface of the patient, but is at a distance from the latter that depends on dosimetric parameters. As a result of this distance, some of the emitted light cone no longer impinges on the treatment area, but impinges on areas that should not be treated and hence have to be covered, or escapes entirely. The consequences of the partly unused light power are increased energy requirements and hence increased energy costs.

An additional disadvantage of this type of equipment arises from the fact that these items of equipment only have one irradiation element, generally in the form of a bar of discrete light sources. These cannot be used to treat a plurality of spaced-apart areas at the same time. To this end, the equipment must in each case be readjusted and the treatment has to be restarted from the outset.

The document U.S. Pat. No. 6,290,713 discloses a flexible light mat for application in PDT—particularly for treating newborns against postnatal hepatitis—with a multiplicity of integrated light-emitting diodes, a diffuser layer for scattering the emitted light and a cooling device with cooling channels to dissipate the generated heat. As a result of its flexibility, the light mat can be wrapped around a body part to be treated of an adult or the torso of an infant.

The cooling device can be operated both with a gaseous (e.g. air) and a liquid medium flowing therethrough, but this substantially only serves to transport away the heat generated by the lamps themselves. By contrast, there is no direct cooling of the upper skin or tissue layers that have been heated by the penetrated radiation.

Additionally, the connection between the cooling of the light mat and an external pump for the coolant via a tube system brings about the dependence on external equipment during the treatment and hence leads to the patient being largely immobile.

The diffuser layer between the light sources and the treatment region contains small lacquer or powder particles, on which the light passing though the layer is strongly scattered. The absorption of light by the particles, which occurs in addition to the scattering effect, leads to a non-negligible power loss of the radiation on the path between light source and treatment region.

U.S. Pat. No. 7,304,201 has disclosed a self-adhesive, wearable bandage for PDT for attachment to a specific area, which bandage has a flexible light-emitter layer and a replaceable light-permeable dressing and can match the shape of the treatment region. The light is backscattered by means of an external cover that reflects on its inner side, but there is no further diffusion effect. The bandage moreover does not have a cooling device.

US 2008/0039906 discloses a light-therapeutic treatment apparatus for body-external and -internal application, with an irradiation unit and an integrated cooling-tube system for dissipating the heat generated by the light sources by means of a liquid coolant. There is neither active cooling of the irradiated skin or tissue layers nor a radiation-guiding effect on the emitted light.

The irradiation unit is shaped such that it is pre-adapted to the treatment region. The cooling-tube system in turn requires an external supply unit—e.g. a pump.

The document U.S. Pat. No. 6,454,789 has disclosed a PDT apparatus, which can be worn by the patient by means of a strap, for an application within the body by means of a cannula and an optical fiber running therein. As a result of the way it is worn and the energy being supplied by means of a battery, the patient obtains extensive mobility. There is no cooling system and no device for homogenizing the radiation field.

An object of the present invention is the provision of a system, designed for application within PDT, with integrated pain management for reducing and avoiding patient pain during radiation treatment.

The pain management by the system should ensure a continuous and pain-free treatment without interruptions.

A further object of the invention is the provision of a substantially isotropic radiation field for PDT, which radiation field can act with almost the same intensity and the same beam cross section on every areal segment of the treatment region.

Furthermore, it is advantageous if the means used for this only result in a small power loss in the influenced radiation of at most 5%.

A homogenized radiation field should be provided for irradiation on a treatment region, the emission region of which radiation field should be comparable to or larger than the currently conventional treatment regions of approximately 20 $cm^2$.

According to the object of the invention, the wavelength spectrum of the applied radiation is flexible in the region suitable for the medical application within the scope of PDT, wherein, by contrast, the wavelength spectrum for a discrete treatment is clearly defined.

A further object of the invention consists in the option of synchronous treatment of a plurality of areas that are at a distance from one another.

Additionally, the present invention should make an irradiation application within the scope of PDT largely independent of medical treatment facilities.

According to the invention, these objects are achieved by implementing the subject matter of independent claims 1 and 14. Features that alternatively or advantageously develop the invention may be gathered from the dependent patent claims.

According to the invention, the irradiation and cooling unit, or an irradiation/cooling combination, is embodied as a modular system with four main components. In the process, according to the invention, a homogenization of the radiation field is brought about by the interaction between the components.

Such a homogenization consists of providing at the cooled passage region a radiation field that has a minimal internal structure, i.e. no or only minimal spatially dependent variations in the intensity. Since the radiation emitted by the individual radiation sources therefore has discrete source points and a usually large divergence, the inner structure impressed by the generation must be reduced or removed.

The divergence results in different angles of incidence on the treatment surface, depending on the position, and yields different luminances, and so an angle of incidence that is as uniform as possible is sought after. This change in divergence can be brought about by a lens effect, which, according to the invention, is brought about by the cooling medium or by the container used as a receptacle. Although complete collimation can be achieved in only very few cases as a result of the dimensions and the distance between source and treatment region, a small lens effect in practice already, exhibits an improvement in the irradiation quality.

A second effect utilized for homogenization consists of returning radiation components, which would otherwise emerge from the beam path, by reflection on the wall. Both effects in combination lead to a more homogeneous radiation field, in which moreover the losses are also reduced by reflection and changing the divergence or focusing, and so a reduction in the thermal load generated by the sources is subsequently also possible in addition to the improved efficiency of the arrangement.

In detail, the main components of the irradiation/cooling combination according to the invention are: at least one irradiation element for emitting the light used within the scope of PDT, at least one cooling element for reducing the pain of the PDT patient, which cooling element at the same time ensures the impact of a homogenized radiation field on the treatment region of the patient as a result of a suitable design, and also a control unit and a power supply unit.

Irradiation element, control unit, and/or power supply unit form a functional assembly and in the process may be embodied both as spatially separated items of equipment and as a modular unit.

As further components, the system has a first fixing device for defined positioning of the irradiation/cooling combination with respect to the treatment region and a second fixing device for attaching the irradiation element to the cooling element. In principle, both fixing devices can also be implemented together in a single fixing device.

During work application within the scope of a PDT application, one side of the cooling element rests against the treatment region with an optical passage region that can be cooled, while a second optical passage region lies against the emission side of the emitted radiation of the irradiation element.

The irradiation element is embodied as a substantially planar arrangement of discrete light sources, which are suitable for continuous and/or pulsed emission of radiation of at least one wavelength for application in PDT. In principle, visible light, near infrared and near ultraviolet can be utilized in PDT.

A preferred embodiment of the invention contains the embodiment of the irradiation element as an LED bar with auxiliary lenses. An airing device dissipates the heat directly produced by the light sources.

The irradiation element is suitable for being attached with its radiation-emergence side to the cooling element, in particular by means of the second fixing device. A preferred embodiment of the invention contains the embodiment of the second fixing device as a clasp or frame.

The dosimetric control, for example setting the duration and intensity of an irradiation, and the selection of one or more wavelengths of the utilized radiation from the irradiation element is brought about by means of a control unit. Here, a control unit can in one embodiment of the invention control a plurality of irradiation elements dependently or independently of one another.

The power supply unit for supplying the energy is suitable for a mobile PDT application and is embodied as a battery in a preferred embodiment of the invention.

The cooling element has a cover and a deformable—more particularly liquid or gel-like—filling medium and is permeable to the emitted radiation in a passage direction thereof.

Substances that are suitable for being precooled as a result of their heat capacity may be used as filling medium. In addition to the permeability to light, the filling medium must have a correspondingly low pour point such that it can be stored in the refrigerator at close to 0° C., more particularly at 4-6° C., without solidifying.

A preferred embodiment of the invention contains the use of viscous white medicinal oils as filling medium for the cooling element, for example "Ondina 941" from "Shell".

The cover of the cooling element has one or more lateral regions, which are substantially oriented in the passage direction of the light and substantially reflect the light on their inner surfaces, and two passage regions, wherein one passage region constitutes the optical passage region that can be cooled and is suitable to rest against the treatment region.

The passage regions of the cooling element may have a design that is either round or has corners, and they have a greater flexibility than the lateral walls as a result of their design. The latter substantially maintain their dimensional stability, for example as a result of their thicker walls compared to the passage regions or as a result of using a material that is more solid per se, when an additional external pressure is applied—particularly after attachment to the treatment region. This makes it possible to define a substantially stable distance between the passage regions by means of the lateral wall height, while the flexible passage region that can be cooled can be adapted to the shape of the treatment region.

If the treatment region is deformed as a result of the cooling element resting against it, the cooling element with its filling medium acts in a divergence-changing fashion on the emitted light (lens effect). Together with the reflection of the light on the inner side of the lateral walls, this brings about a mixing of the radiation passing through and makes it isotropic. The light emerging from the optical passage region that can be cooled and acting on the treatment region is therefore largely homogenized.

As a result of the flexibility of the passage region and the radiation field, which emerges therefrom and is homogenized as a result of the aforementioned effects, larger treatment regions are now accessible per irradiation unit.

The cooling element is precooled to a temperature of approximately 4-6° C. in a cooling device, for example a refrigerator, before a PDT treatment of the patient and, at this temperature that a patient still considers comfortable, applied to the treatment region, more particularly the skin, with its optical passage region that can be cooled. The cooling element remains against the treatment region during the entire irradiation procedure, which on average takes up to 20 minutes, and thereby, with the aid of continuous cooling, prevents the treated region and the tissue situated therebelow from being able to heat up to a temperature that is considered uncomfortable or even painful by the patient. In order to ensure a sufficiently long cooling effect, the cooling element must contain a filling medium that, in terms of amount and heat capacity, is suitable for providing a subsequent cooling power as a result of precooling that allows the desired temperatures on the skin surface over the entire period of application. A deformable, more particularly liquid or gel-like, filling medium suitable for being precooled thus has the required heat capacity in respect of application parameters, volume, and heat passage region of the cooling element.

The first fixing device suitable for defined positioning of the irradiation/cooling combination with respect to the treatment region is embodied as a closable strap, in particular with a hook-and-loop fastener, in a preferred embodiment of the invention. One or more cooling elements are directly attached to the strap, wherein the strap is suited to being worn on the body by the patient. Furthermore, a plurality of straps with cooling elements attached directly thereon can at the same time be applied to the body of the patient and can be worn by the latter, and so there may be a synchronous PDT treatment of spaced-apart treatment regions.

The embodiment of the irradiation/cooling combination according to the invention as a wearable and hence mobile system ensures that the patient is largely mobile. As a result of the combination of mobility with the integrated pain management system, the patient requires substantially no support from medical staff and is independent of treatment facilities. The PDT application can be carried out anywhere and without supervision by the patient him-/herself.

The preferred embodiment of the invention contains the use of films made of thermoplastic polyurethane ester or ether for the cover of the cooling element and the fixing strap, for example "Sarna Plastec 2201" or "Sarna Plastec 4201" from "Sarna Plastec" (Samen, Switzerland).

Here, the cooling element ("gel-pad") is welded onto a polymer strap, which has a hook-and-loop fastener (Velcro male/female) that is suitable for fixing the gel-pad on the body surface together with the irradiation element.

A mechanical fixation of the device according to the invention on the treatment region can be implemented both directly on the cooling element and indirectly on the irradiation element; the latter in the process at the same time brings about the defined positioning of the cooling element with respect to the treatment region by means of the second fixing device.

By way of example, the fixation of the cooling element by means of an adhesive bandage directly on the treatment region and the fixation of the cooling and irradiation elements by means of a wrap bandage are feasible as further embodiments of the invention.

As a result of using the irradiation/cooling combination according to the invention in PDT, an effective pain management is available for the patient whilst largely freeing the latter from pain caused by the treatment. In conjunction with this, provision is made for a compact mobile PDT treatment system with complete mobility and independence for the patient and larger treatment regions per irradiation unit.

Figure 1:
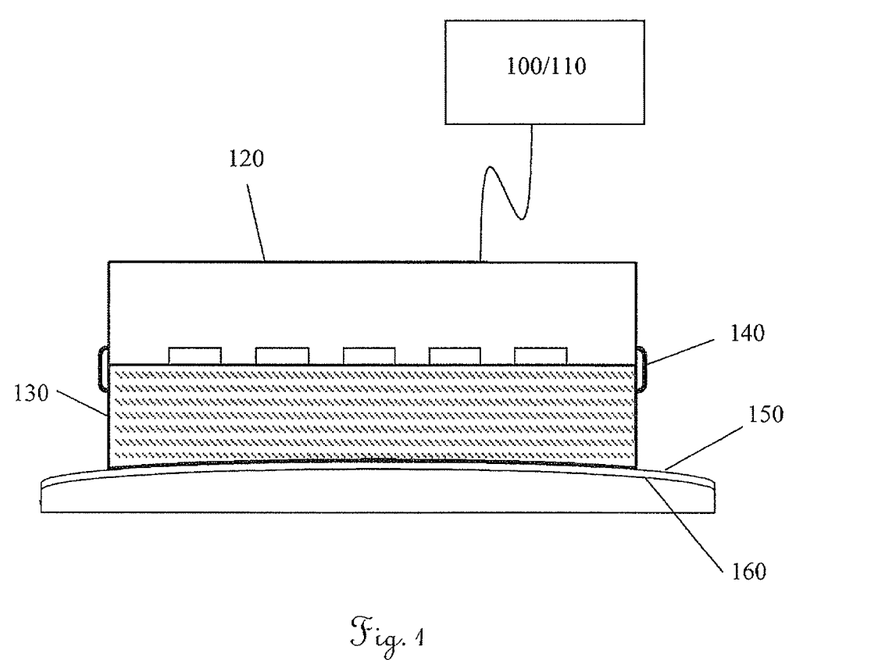
FIG. 1 shows a sectional view of a (schematic) irradiation/cooling combination according to the invention that rests against the treatment region.

The device according to the invention and the method according to the invention will be described in more detail below on the basis of the figures. In detail:

FIG. 1 illustrates an irradiation/cooling combination according to the invention, placed against the treatment region. The attachment thereof to the treatment region is brought about by means of a first fixing device.

The irradiation element 120 connected to the power supply unit 100 and control unit 110 is attached to the cooling element 130 by means of a second fixing device 140. The cooling element 130 in turn is welded onto a carrying strap 150, which in this embodiment of the invention constitutes the aforementioned first fixing device and fixes it on the treatment region 160.

By way of example, the second fixing device 140 may be embodied as a clasp or frame.

As a result of its design, the cooling element 130 is deformable and can be adapted to the treatment region 160.

Figure 2:
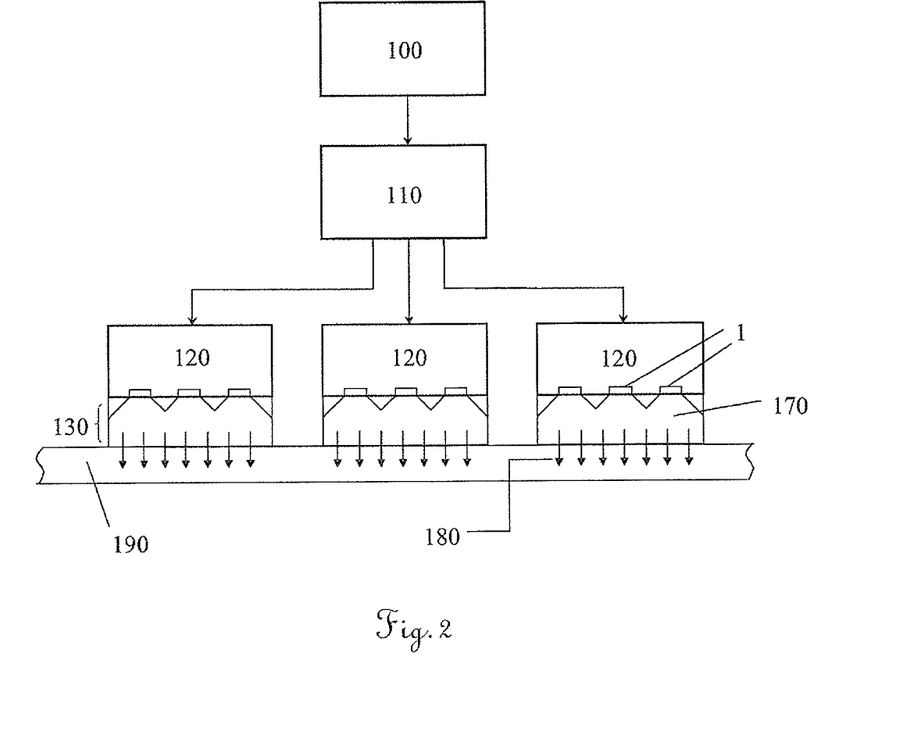
FIG. 2 shows an irradiation/cooling combination according to the invention in the modular design thereof.

The modular design of the irradiation/cooling combination according to the invention may be gathered from the schematic illustration in FIG. 2.

The control unit 110, which controls one or more irradiation elements 120 in a dosimetric fashion, is supplied with energy by means of the power supply unit 100. The irradiation elements 120 in turn are attached to the cooling elements 130 by means of a fixing device (not illustrated).

The light-emitting diodes 1 of the irradiation unit 130 each emit a radiation field 170. The radiation thereof is mixed within the cooling element 130 as a result of reflection and the lens effect, and so substantially homogenized radiation 180 impinges on the treatment region and penetrates the tissue 190 situated therebelow.

Figure 3A:
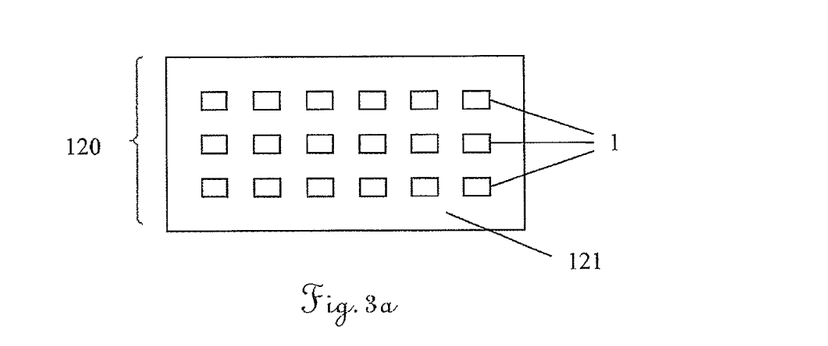
FIGS. 3a/b show a schematic illustration of an irradiation element with an LED light bar.
Figure 3B:
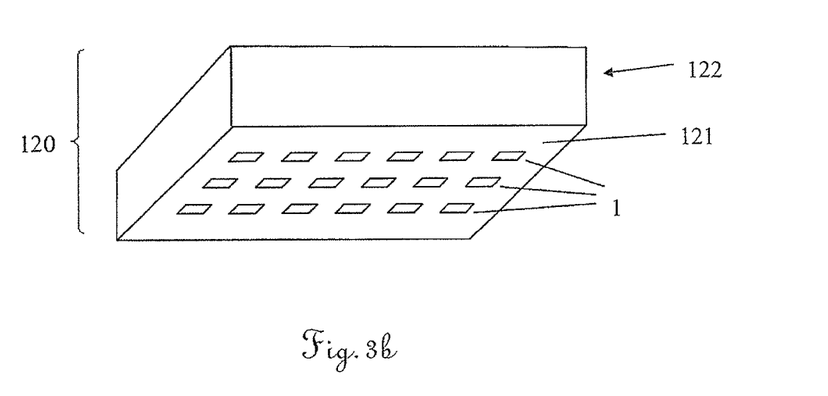

FIGS. 3a and 3b schematically show an irradiation element with a bar of light-emitting diodes (LED) 1. FIG. 3a shows the radiation emission region 121 with the LED bar in a plan view, FIG. 3b shows the irradiation element 120 and the housing 122 thereof, as well as the radiation emission region 121 with the LEDs 1 in an oblique view. Here the light sources in the LED bar are arranged in a matrix-like fashion.

Figure 4A:
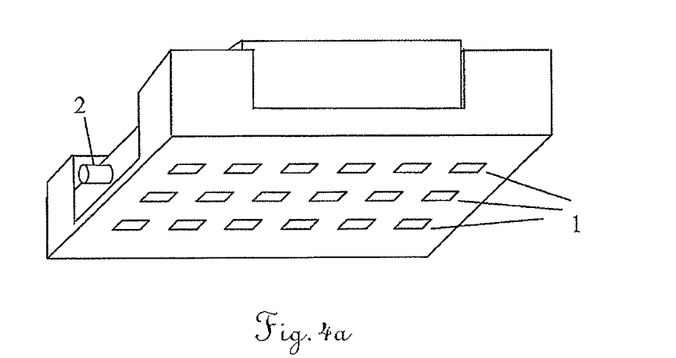
FIGS. 4a/b show a schematic illustration of an opened irradiation element without cover.
Figure 4B:
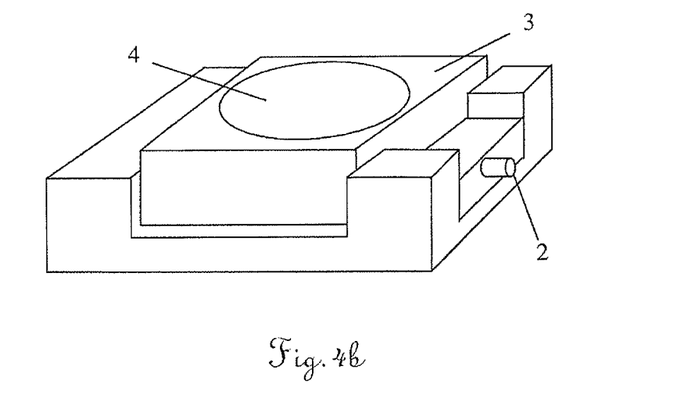

FIGS. 4a and 4b show an opened irradiation element after the cover has been removed. In addition to the LEDs 1, said irradiation element has a current connector 2 and a cooling body 3 with a ventilation inlet 4. In FIG. 4a, the observer looks obliquely in the direction of the radiation emission region, in FIG. 4b obliquely in the direction of the removed cover onto the irradiation element.

Figure 5:
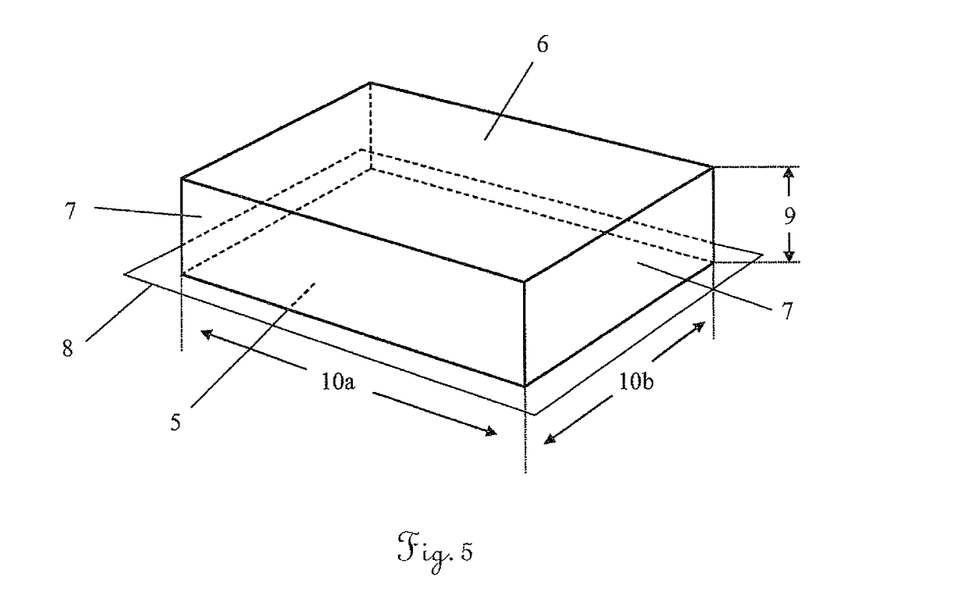
FIG. 5 shows a cooling element in an oblique view.

The cooling element illustrated in FIG. 5 is embodied as a gel-pad with a plastic cover that consists of the optical passage regions 5 and 6, as well as the lateral regions 7. Here the two passage regions 5 and 6 substantially have the same surface area and are arranged substantially parallel to one another.

The illustrated cooling element is one with a rectangular shape of the passage regions. However, in principle these can also be embodied as different polygons, or as circular or elliptical shapes.

The passage region 5 corresponds to the optical passage region that can be cooled and is embodied to be welded to a plastic carrier strap. To this end, as illustrated in FIG. 5, the optical passage region 5 that can be cooled may be provided with an edge 8.

The second passage region 6 rests against the radiation emission region of the irradiation element during a PDT treatment.

The respective lateral regions 7 have the same height 9 but may in principle have both the same and different widths 10a and 10b, and hence may have different surface areas. Here the height 9 of the lateral regions is less than the shortest geometric axis of the passage regions. In the case of a rectangular passage region, this axis constitutes the shorter width 10b of the lateral regions 7; in the case of for example elliptically shaped passage regions, it is the semi-minor axis of the ellipse.

In order to increase the reflectivity, the lateral regions of the cooling element may be polished, smoothed, coated, or vaporized.

Figure 6:
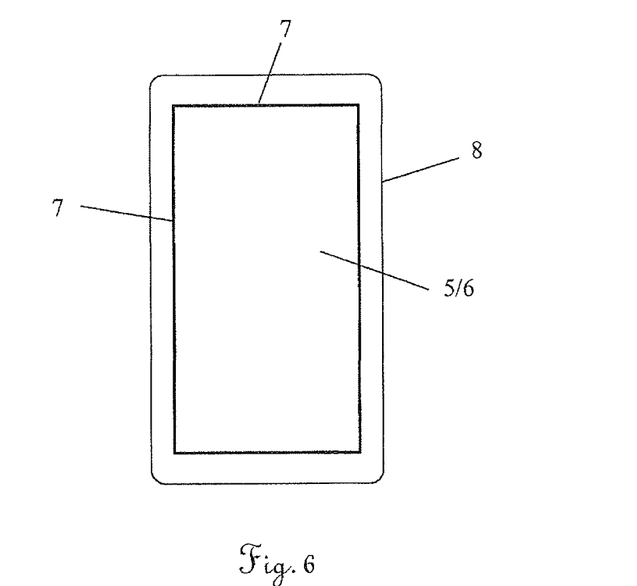
FIG. 6 shows a cooling element in the viewing direction of the passage direction of the radiation.

FIG. 6 shows the cooling element with the two passage regions 5 and 6, the edge 8 of the region 5 and the lateral regions 7 in the passage direction of the emitted radiation.

Figure 7A:
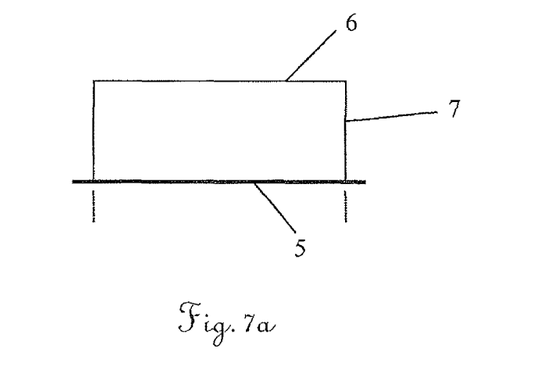
FIGS. 7a/b show a lateral view of a cooling element.
Figure 7B:
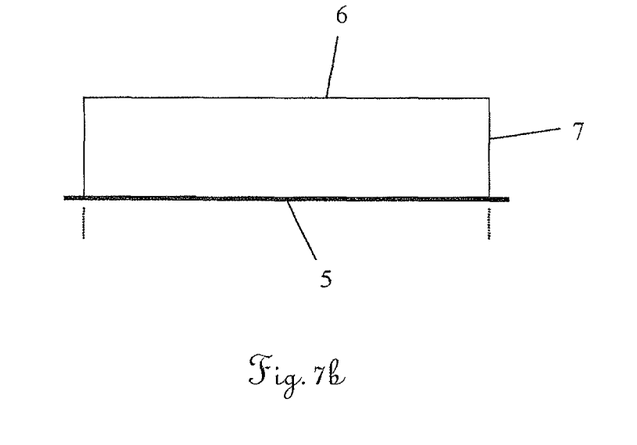

FIGS. 7a and 7b show the cooling element with the two passage regions 5 and 6 and the lateral regions 7 in two different lateral views.

The region 5 is the optical passage region that can be cooled.

Figure 8:
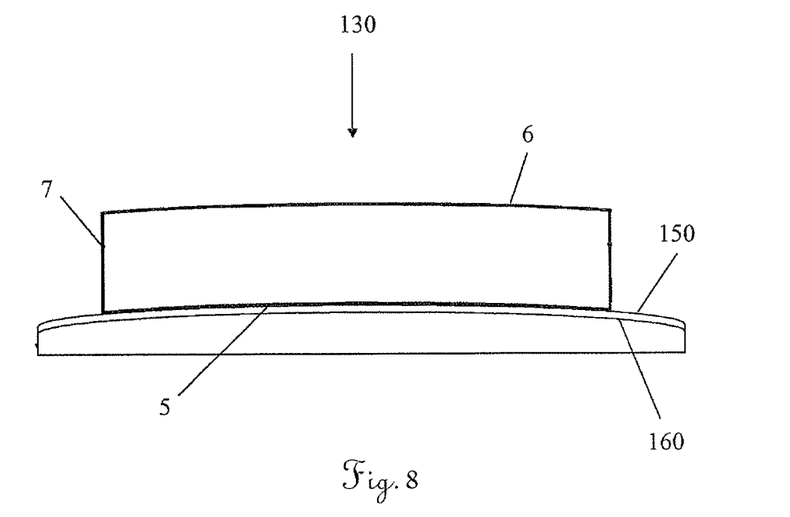
FIG. 8 shows a cooling element with its deformable passage regions for the radiation.

The flexibility of the cooling element 130 can be identified in FIG. 8. In the illustrated case, said cooling element is fixed to the treatment region (skin) 160 by means of the carrying strap 150.

As a result of their design, the passage regions 5 and of the cooling element have, as a functional component, flexibility in the case of an additional external pressure that is generated by the fixation. This allows the optical passage region 5 that can be cooled to be adapted to the shape of the treatment region 160; the second passage region 6 designed to rest against the emission side of an irradiation element can be equally deformed.

By contrast, the lateral regions 7 of the cooling element 130 substantially maintain their shape in the aforementioned situation as a result of their design and, as a functional component, have a lower deformability than the passage regions 5 and 6.

Figure 9A:
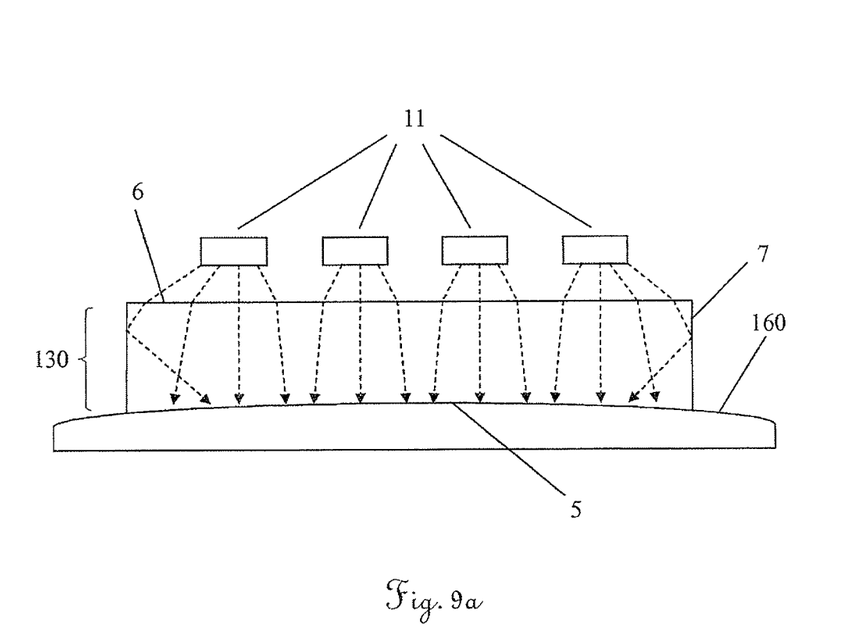
FIG. 9a shows a possible course of the radiation within the cooling element.

FIG. 9a reproduces a possible course of the radiation within the cooling element (gel-pad) 130. The radiation emitted by the light sources 11 passes through the passage region 6 into the interior of the cooling element 130, which is deformed as a result of resting against the convexly arced skin surface 160, is mixed by the lens effect thereof and by the reflection at the inner side of the lateral walls 7, and finally reemerges largely homogenized out of the now arced optical passage region 5 that can be cooled.

Depending on the specific embodiment and the given geometric conditions, the beam paths for the individual light sources 11 cross and hence there is mixing of the radiation, which supports homogenization and, if necessary, prevents the creation of entirely unilluminated zones even if one light source 11 fails.

Figure 9B:
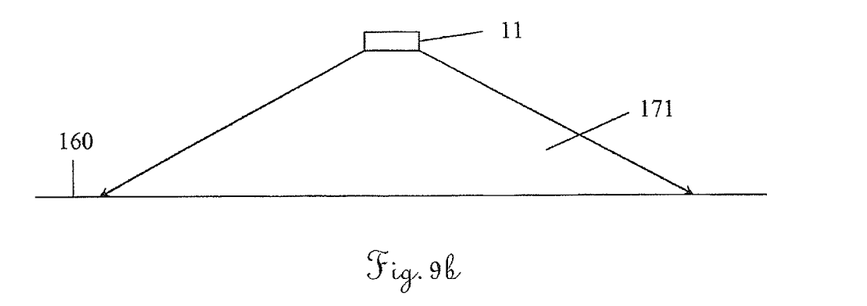
FIG. 9b shows a course of the radiation without inserted optical means.
Figure 9C:
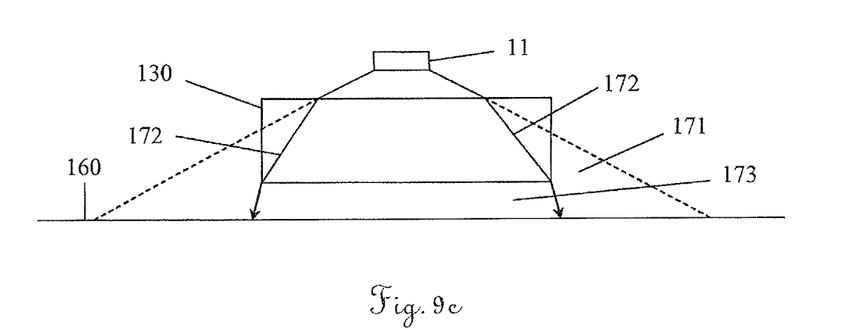
FIG. 9c shows the beam path being influenced by the collimating effect of the cooling element.
Figure 9D:
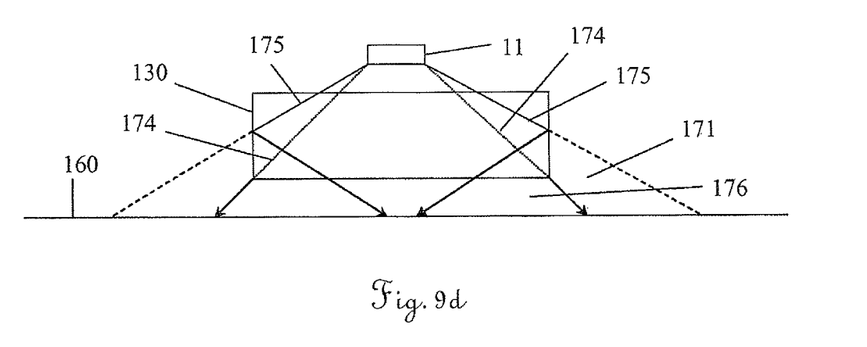
FIG. 9d shows the beam path being influenced by the reflection of the radiation at the lateral walls of the cooling element.

The course of the radiation emitted from a light source of the irradiation element may be gathered schematically from FIGS. 9b, 9c and 9d.

The goal of homogenizing the radiation consists of providing it without internal structure at the optical passage region 5 that can be cooled, i.e. with an intensity profile that is as uniform as possible and has a direction of incidence that is as perpendicular as possible to the skin surface 160 or the optical passage region 5 that can be cooled.

The uninfluenced radiation field 171 impinges on the treatment region 160 in FIG. 9b.

FIG. 9c illustrates the collimating effect (lens effect) of the cooling element 130. The light beams 172 delimiting the previously uninfluenced radiation field 171 to the outside are deflected and delimit the significantly narrower light cone of the resultant radiation field 173.

FIG. 9d illustrates the effect of the reflection of the radiation at the inner sides of the lateral walls of the cooling element 130. The beams emerging from the light source 11 outside of the light cone delimited by the light beams 174 are substantially reflected at the lateral walls and impinge on the treatment region 160 within the light cone of the resultant radiation field 176. The beam path of the light beams 175 delimiting the light cone of the uninfluenced radiation field 171 is illustrated as an example for this.

The influences on the beam path described individually in FIGS. 9c and 9d for reasons of clarity in actual fact occur simultaneously and together bring about a change in the beam cross section. The aforementioned effects each have a different weighting in terms of their effect, depending on the precise embodiment of the cooling element.

Figure 10:
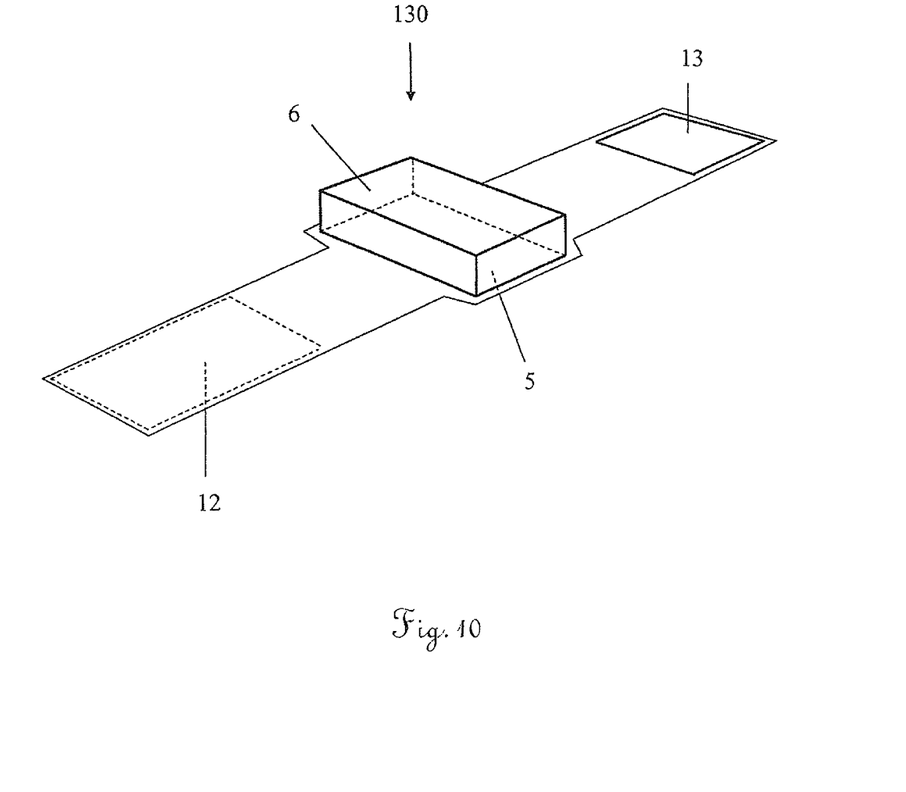
FIG. 10 shows an oblique view of a cooling element attached to a fixing strap.

FIG. 10 shows, welded onto a carrying strap, a cooling element 130 with its passage regions 5 and 6 in an oblique view. The carrying strap has two hook-and-loop fasteners 12 and 13.

The region 5 is the optical passage region that can be cooled.

The cooling element can be fixed on the body surface of the patient, for example to the torso or to the extremities, by means of the carrying strap.

In one embodiment of the invention (not illustrated), a plurality of cooling elements are welded onto a carrying strap next to one another.

Figure 11:
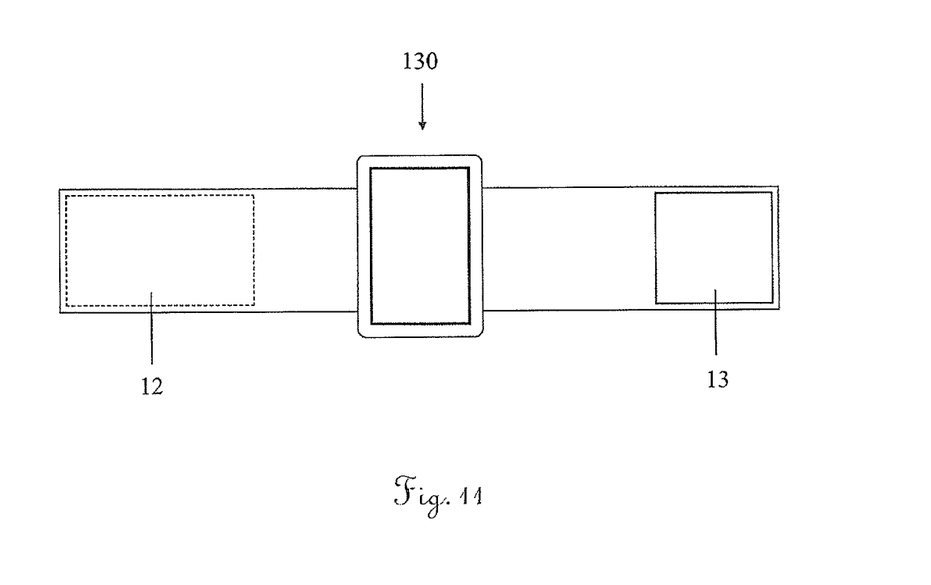
FIG. 11 shows (in the passage direction of the radiation) a plan view of a cooling element attached to a fixing strap.

FIG. 11 shows, in the passage direction of the emitted radiation, a cooling element 130 that is welded onto a carrying strap provided with two hook-and-loop fasteners 12 and 13.

Figure 12:
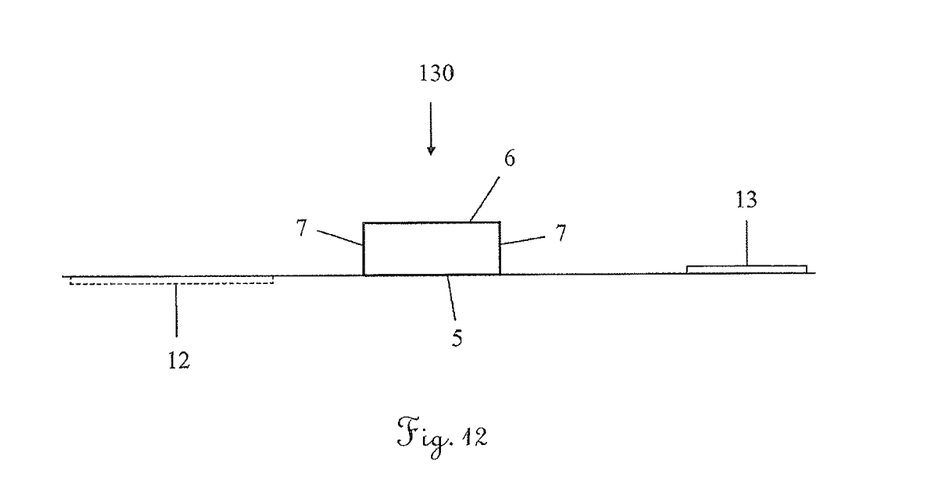
FIG. 12 shows a lateral view of a cooling element attached to a fixing strap.

FIG. 12 shows, in a lateral view, a cooling element 130 that is welded onto a carrying strap provided with two hook-and-loop fasteners 12 and 13.

The cooling element has the passage regions 5 and 6, and also the lateral regions 7. The region 5 is the optical passage region that can be cooled.

The invention claimed is:

1. An irradiation/cooling combination for application in a photodynamic therapy, more particularly an application of a photosensitizer, with
   an irradiation element with an emission direction for a radiation to be emitted,
   a cooling element, wherein the latter
      is designed to be attached between the irradiation element and a treatment region, more particularly the skin surface of a patient,
      is permeable to the emitted radiation in a passage direction,
      has an optical passage region, which can be cooled, for the radiation as an attachment to the treatment region and a second passage region as an attachment to the irradiation element,
   a first fixing device for defined positioning of the irradiation/cooling combination with respect to the treatment region,
   wherein
the cooling element has
   at least one lateral region, wherein the latter
      is oriented substantially perpendicular to the passage regions and
      is embodied such that the lateral region is less flexible than the passage regions,
      predefines a spacing between the passage regions by means of a given height of the lateral region, wherein this spacing remains substantially constant under the application of an additional external pressure that is created during the fixation,
      is designed to reflect the emitted radiation,
   a filling medium that can be suitably deformed for being precooled, more particularly a liquid or gel-like filling medium,
wherein the cooling element is deformable, which can be brought about as a result of being attached to the treatment region, and so this results in homogenization of the radiation within the cooling element by means of a divergence-changing effect on a beam cross section of the emitted radiation.

2. The irradiation/cooling combination as claimed in claim 1,
   wherein a control unit for limiting an irradiation duration and intensity, and for selecting one or more wavelengths of the radiation emitted by the irradiation element, and more particularly a power supply unit for supplying a voltage.

3. The irradiation/cooling combination as claimed in claim 1,
   wherein
   the irradiation element is embodied as an LED module with auxiliary lenses.

4. The irradiation/cooling combination as claimed in claim 1,
   wherein
   the at least one lateral region of the cooling element is polished, smoothed, coated, or vaporized in order to increase the reflectivity thereof.

5. The irradiation/cooling combination as claimed in claim 1, wherein
the irradiation element is embodied to emit electromagnetic radiation with at least one wavelength in the spectrum of visible light and the near infrared and ultraviolet region.

6. The irradiation/cooling combination as claimed in claim 2,
wherein
irradiation element, control unit, and power supply unit are embodied
in each case as spatially separable individual pieces of equipment embodied as a module and/or
as an overall unit consisting of a plurality of the aforementioned individual pieces of equipment.

7. The irradiation/cooling combination as claimed in claim 1,
wherein in each case one cooling element and one irradiation element form a common irradiation module, wherein a plurality of these irradiation modules can be associated with a common control unit.

8. The irradiation/cooling combination as claimed in claim 7,
wherein a plurality of irradiation modules can be regulated independently of one another by means of the control unit.

9. The irradiation/cooling combination as claimed in claim 1,
wherein the cooling element is embodied as a gel-pad with a cover of a plastic film, more particularly a polyurethane film, that is substantially dimensionally stable in the absence of additional external pressure.

10. The irradiation/cooling combination as claimed in claim 1,
wherein the cooling element is embodied as a gel-pad with a filling medium made of a viscous medicinal oil that is permeable to visible light and has a solidification point of less than 0° C.

11. The irradiation/cooling combination as claimed in claim 1,
wherein the passage regions of the cooling element are, due to their design, deformable after attachment of the irradiation/cooling combination to the treatment region, more particularly as a result of
the ratio of the lateral lengths of the cooling element with respect to one another, wherein, more particularly, the height of the lateral regions is less than the length of the shortest geometric axis of the passage regions,
the ratio of the surface areas of the passage regions and the lateral regions of the cooling element with respect to one another, wherein, more particularly, the sum of the surface areas of the lateral regions is less than the sum of the surfaces areas of the passage regions,
different wall thicknesses of the lateral and passage regions, wherein, more particularly, the wall thickness of the lateral regions is greater than the wall thickness of the passage regions, and/or
different materials of the lateral and passage regions, wherein, more particularly, the material of the lateral region per se has a lower flexibility than the material of the passage regions.

12. The irradiation/cooling combination as claimed in claim 1,
wherein a second fixing device for attaching the irradiation element to the cooling element, more particularly wherein said second fixing device is embodied as a clasp or frame.

13. The irradiation/cooling combination as claimed in claim 1,
wherein a strap, more particularly a polymer strap, for attaching at least the cooling element to the treatment region, more particularly wherein the cooling element is welded onto the strap.

14. A method for generating a homogenized radiation field at an optical passage region that can be cooled, more particularly with an irradiation/cooling combination as claimed in claim 1, with
generation of a radiation field by a multiplicity of discrete radiation sources,
guiding of the radiation through a cooling element, wherein the optical passage region constitutes an external surface of the cooling element,
characterized in that wherein
the radiation field is homogenized by
changing the divergence of the radiation by means of a lens effect caused by a deformation of the cooling element,
reflecting the radiation on the lateral regions of the cooling element,
more particularly with at least partial mixing of the beam path.

15. The method as claimed in claim 14, wherein a precooling of the cooling-optical element, more particularly to a temperature of 4-6° C., directly before attaching the cooling element to a treatment region.

* * * * *